US006392039B1

(12) United States Patent
Aulombard et al.

(10) Patent No.: US 6,392,039 B1
(45) Date of Patent: May 21, 2002

(54) METHOD FOR PREPARING (R)-(+)-3 {1-[2-(4-BENZOYL-2(3, 4-DIFLUOROPHENYL) MORPHOLIN-2-YL)ETHYL]-4-PHENYLPIPERIDIN-4-YL}-1,1-DIMETHYLUREA, ITS SALTS SOLVATES AND/OR HYDRATES

(75) Inventors: Alain Aulombard, Lattes; Francoise Bernon, Saint Clément la Rivière; Sabrina Bonnefoy, Sommieres, all of (FR); Alain Burgos, Exton, PA (US); Claude Cabos, Juvignac; Eric Lucas, La Boissière, both of (FR)

(73) Assignee: Sanofi-Synthelabo, Paris (FR)

( * ) Notice: Subject to any disclaimer, the term of this patent is extended or adjusted under 35 U.S.C. 154(b) by 0 days.

(21) Appl. No.: 09/868,562

(22) PCT Filed: Dec. 14, 1999

(86) PCT No.: PCT/FR99/03123

§ 371 Date: Jun. 19, 2001

§ 102(e) Date: Jun. 19, 2001

(87) PCT Pub. No.: WO00/39126

PCT Pub. Date: Jul. 6, 2000

(30) Foreign Application Priority Data

Dec. 23, 1998 (FR) ............................................ 98 16410

(51) Int. Cl.$^7$ ...................... C07D 265/30; C07D 413/06
(52) U.S. Cl. ......................................... 544/130; 544/158
(58) Field of Search ................................. 544/130, 158

(56) References Cited

U.S. PATENT DOCUMENTS

| 5,641,777 A | 6/1997 | Emonds-Alt et al. |
| 5,741,910 A | 4/1998 | Bichon et al. |
| 5,780,466 A | 7/1998 | Emonds-Alt et al. |
| 5,869,663 A | 2/1999 | Emonds-Alt et al. |
| 5,942,523 A | 8/1999 | Bichon et al. |
| 5,977,359 A | 11/1999 | Emonds-Alt et al. |

FOREIGN PATENT DOCUMENTS

| EP | 0673928 | 9/1995 |
| WO | WO 96/23787 | 8/1996 |
| WO | WO 97/10211 | 3/1997 |

OTHER PUBLICATIONS

Derwent Patent Abstract No. 199718 (2001).

*Primary Examiner*—Robert W. Ramsuer
(74) *Attorney, Agent, or Firm*—Michael D. Alexander; Paul E. Dupont

(57) ABSTRACT

The invention relates to a process for preparing (R)-(+)-3-{1-[2-(4-benzoyl-2-(3,4-difluorophenyl)-morpholin-2-yl) ethyl]-4-phenylpiperid-4-yl}-1,1-dimethylurea and the salts, solvates and/or hydrates thereof.

36 Claims, No Drawings

METHOD FOR PREPARING (R)-(+)-3 {1-[2-(4-BENZOYL-2(3, 4-DIFLUOROPHENYL)MORPHOLIN-2-YL)ETHYL]-4-PHENYLPIPERIDIN-4-YL}-1,1-DIMETHYLUREA, ITS SALTS SOLVATES AND/OR HYDRATES

This application is a 371 of PCT/FR99/03123 filed Dec. 14, 1999.

The present invention relates to a novel process for preparing (R)-(+)-3-{1-[2-(4-benzoyl-2-(3,4-difluorophenyl)morpholin-2-yl)ethyl]-4-phenylpiperid-4-yl}-1,1-dimethylurea and the salts, solvates and/or hydrates thereof.

(R)-(+)-3-{1-[2-(4-Benzoyl-2-(3,4-difluorophenyl)morpholin-2-yl)ethyl]-4-phenylpiperid-4-yl}-1,1-dimethylurea, of formula:

(I)

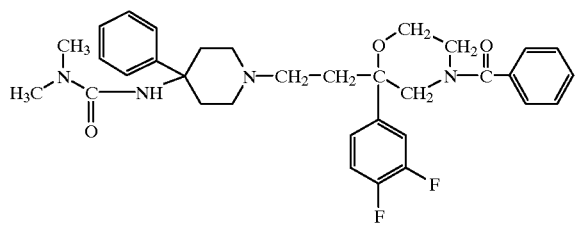

referred to hereinbelow as compound A, is a novel powerful and selective non-peptide antagonist of the $NK_2$ receptors of neurokinin A in various species, in particular of the human $NK_2$ receptors (X. Emonds-Alt et al., Neuropeptides, 1997, 31 (5), 449–458) and, consequently, may be useful especially in the treatment of complaints of the respiratory, gastro-intestinal, urinary, immune or cardiovascular system and of the central nervous system, and also for pain and migraine.

The preparation of compound A is illustrated in international patent application WO 96/23787. According to said document, compound A is prepared by reacting (+)-4-benzoyl-2-(3,4-difluorophenyl)-2-[2-(methanesulfonyloxy)ethyl]morpholine (compound B) with 3-(4-phenylpiperid-4-yl)-1,1-dimethylurea para-toluenesulfonate (compound C), in the presence of potassium carbonate, followed by conversion to its hydrochloride. However, this process has disadvantages and drawbacks, which are sufficient to exclude it from any use on an industrial scale.

For example, compound A prepared by this process is obtained in a relatively low yield, of about 38% calculated on the basis of compound B, according to the description of patent application WO 96/23787.

The main reason for this low yield is the formation, during the reaction of compound B with compound C, of numerous impurities in the reaction medium, leading to a low yield for conversion to compound A. It has been possible to isolate and identify these impurities, the main one of which (compound D) has the formula:

(II)

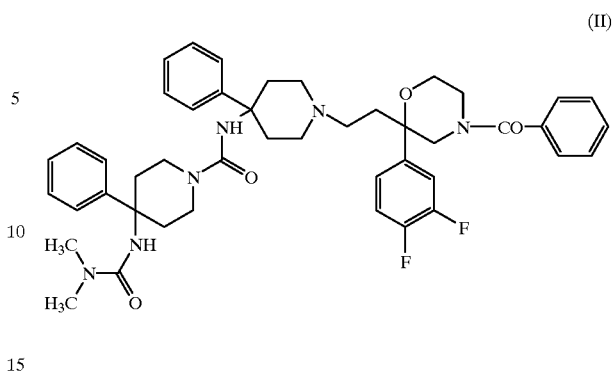

It has been found that the formation of these impurities, especially of compound D, is due to the instability of compound C in the form of the free base in solution. Thus, a stability study carried out on compound C at 50° C. in acetonitrile shows that it rapidly decomposes (about 5% per hour) and gives a multitude of products corresponding to a polymerization (dimer, trimer, etc.), thus excluding the use of compound C on an industrial scale.

Furthermore, the presence of these impurities, in particular of compound D, in the reaction medium, makes it difficult to separate out and purify compound A.

Consequently, the search for a process to prepare compound A which does not have the drawbacks and disadvantages of the known prior art process remains of unquestionable interest.

A novel process for preparing compound A which uses stable starting materials and intermediate compounds in the operating conditions, and which does not lead to the formation of the impurities present during the prior art process, has now been found.

Thus, according to one of its aspects, a subject of the present invention is a process for preparing (R)-(+)-3-{1-[2-(4-benzoyl-2-(3,4-difluorophenyl)morpholin-2-yl)ethyl]-4-phenylpiperid-4-yl}-1,1-dimethylurea, and the salts, solvates and/or hydrates thereof, of formula:

(I)

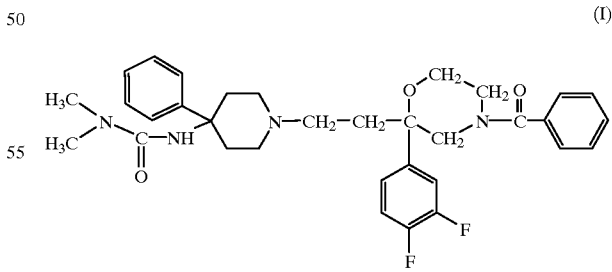

characterized in that:

(+)-4-benzoyl-2-(3,4-difluorophenyl)-2-(2-benzenesulfonyloxyethyl)morpholine of formula:

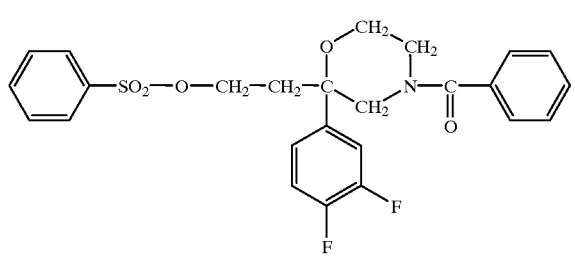

(III)

is reacted, in the presence of a base, with tert-butyl (4-phenylpiperid-4-yl)carbamate of formula:

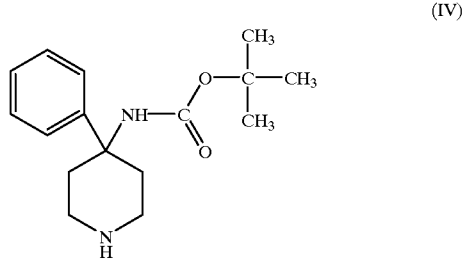

(IV)

to give tert-butyl (+)-(1-{2-[4-benzoyl-2-(3,4-difluorophenyl)morpholin-2-yl]ethyl}-4-phenylpiperid-4-yl)carbamate, of formula

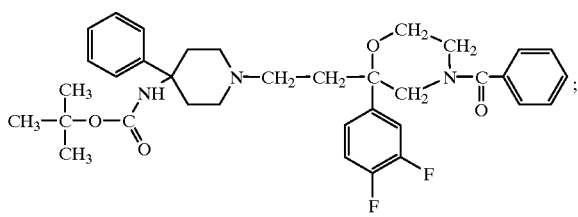

(V)

the compound of formula (V) thus obtained is deprotected by the action of an acid, to give (+)-[2-[2-(4-amino-4-phenylpiperid-1-yl)ethyl]2-(3,4-difluorophenyl)morpholin-4-yl]phenylmethanone, of formula

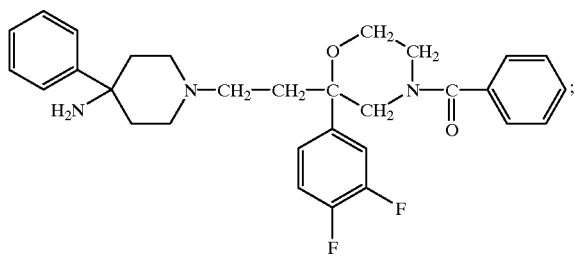

(VI)

c) the compound of formula (VI) thus obtained is reacted first with a reactive derivative of carbonic acid, in the presence or absence of base, and then with dimethylamine to give the expected compound of formula (I);

d) the compound of formula (I) thus obtained is optionally converted into a salt thereof with pharmaceutically acceptable mineral or organic acids.

In the process according to the invention, it is possible to combine two or more steps.

Thus, for example, steps a) and b) may be combined in order to give compound (VI) directly from the compound of formula (III). Similarly, steps c) and d) may be combined. It is also possible to combine all the steps of the process according to the invention, which means that all the steps are carried out without isolating the intermediate compounds of formulae (V) and (VI), thereby simplifying the process.

Salts of the compounds of formula (V) or (VI) and also of the compound of formula (I) may be formed. These salts comprise not only those with mineral or organic acids which allow a suitable separation or crystallization of the compounds of formula (V), (VI) or (I), but also those which form pharmaceutically acceptable salts with the compound of formula (I), such as the hydrochloride, hydrobromide, sulfate, hydrogen sulfate, dihydrogen phosphate, methane sulfonate, methyl sulfate, maleate, fumarate, succinate, 2-naphthalenesulfonate, glyconate, gluconate, citrate, isethionate, benzenesulfonate or para-toluenesulfonate.

Compound A thus obtained may be subsequently separated from the reaction medium according to the conventional methods.

Compound A obtained is isolated in the form of the free base or of a salt thereof, for example the hydrochloride, the fumarate or the succinate. It is also possible to isolate, for example, compound A in the form of the fumarate and to convert it into another of its salts, first by neutralizing it then by treating the free base with an acid, for example succinic acid.

When compound A is obtained in the form of the free base, the salification is carried out by treatment with the chosen acid in an organic solvent. By treating the free base, dissolved, for example, in an ether such as diethyl ether or in an alcohol such as methanol, ethanol or 2-propanol, or in acetone, or in dichloromethane or in ethyl acetate, with a solution of the chosen acid in one of the abovementioned solvents, the corresponding salt is obtained, which is isolated according to the conventional techniques.

Thus, the hydrochloride, hydrobromide, sulfate, hydrogen sulfate, dihydrogen phosphate, methanesulfonate, methyl sulfate, benzenesulfonate, para-toluenesulfonate, oxalate, maleate, succinate, fumarate, 2-naphthalenesulfonate, glyconate, gluconate, citrate or isethionate is prepared, for example.

Preferably, the process according to the invention is used to prepare compound A in the form of the succinate or fumarate.

Thus, compound A in the form of the free base, dissolved in acetone, is treated at room temperature with succinic acid dissolved in acetone and the corresponding succinate is obtained, which is isolated according to the conventional techniques.

Similarly, compound A, in the form of the free base, dissolved in acetone, is treated under hot conditions with fumaric acid in acetone to give, after cooling to room temperature, the corresponding fumarate which is isolated according to the conventional techniques.

(R)-(+)-3-{1-[2-(4-Benzoyl-2-(3,4-difluorophenyl)morpholin-2-yl)ethyl]-4-phenylpiperid-4-yl}-1,1-dimethylurea succinate is novel and forms part of the invention.

(R)-(+)-3-{1-[2-(4-Benzoyl-2-(3,4-difluorophenyl)morpholin-2-yl)ethyl]-4-phenylpiperid-4-yl}-1,1-dimethylurea fumarate is novel and forms part of the invention.

When compound A is obtained in the form of a salt thereof, for example the hydrochloride or the fumarate, the free base may be prepared by neutralizing said salt with a mineral or organic base, such as sodium hydroxide or triethylamine, or with an alkali metal carbonate or bicarbonate, such as sodium or potassium carbonate or bicarbonate, according to the conventional methods.

When carrying out the process according to the invention, it is possible to obtain compound A or a salt thereof in a final yield of about 55% to 70% calculated relative to the starting compound of formula (III).

A subject of the present invention is thus a process for preparing (R)-(+)-3-{1-[2-(4-benzoyl-2-(3,4-difluorophenyl)morpholin-2-yl)ethyl]-4-phenylpiperid-4-yl}-1,1-dimethylurea, and the salts, solvates and/or hydrates thereof, of formula:

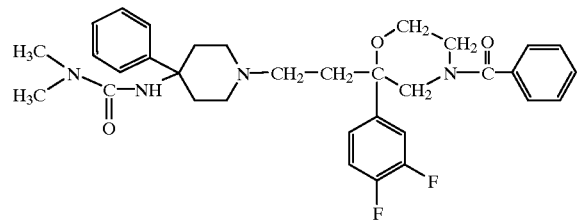

(I)

characterized in that (+)-[2-[2-(4-amino-4-phenylpiperid-1-yl)ethyl]-2-(3,4-difluorophenyl)morpholin-4-yl]phenylmethanone, of formula:

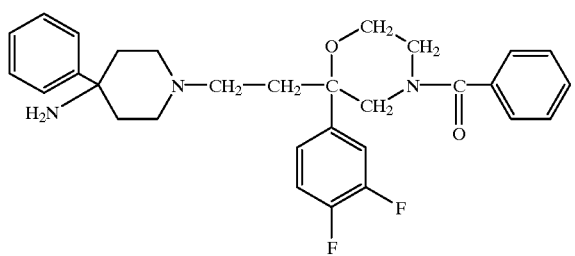

(VI)

is reacted, in an inert solvent, first with a reactive derivative of carbonic acid in the presence or absence of base, and then with dimethylamine, and the compound of formula (I) thus obtained is optionally converted into a salt thereof with pharmaceutically acceptable mineral or organic acids.

Among the reactive derivatives of carbonic acid that are preferred are 1,1'-carbonyldiimidazole, phosgene and p-nitrophenyl chloroformate.

It is particularly preferred according to the invention to use 1,1'-carbonyldiimidazole.

The reactive derivative of carbonic acid is used in the reaction in a proportion of from 1 to 3 molar equivalents per molar equivalent of compound of formula (VI), preferably from 1 to 2 molar equivalents.

When 1,1'-carbonyldiimidazole is used, the reaction is carried out in the absence of base. When phosgene or p-nitrophenyl chloroformate is used, the reaction is carried out in the presence of an organic base such as triethylamine, N,N-diisopropylethylamine or N-methylmorpholine; triethylamine is preferably used.

The base is used in the reaction in a proportion of from 1 to 6 molar equivalents per molar equivalent of reactive derivatives of carbonic acid.

The dimethylamine is used in the reaction in a proportion of from 1 to 6 molar equivalents per molar equivalent of compound of formula (VI) and preferably from 1 to 4 molar equivalents.

The inert solvent may be, for example, a $C_1$-$C_4$ haloaliphatic hydrocarbon such as dichloromethane, 1,2-dichloroethane, chloroform or carbon tetrachloride. Dichloromethane is a preferred solvent.

The inert solvent is used in a proportion of from 2 to 15 equivalents by volume per equivalent by weight of compound of formula (VI). The solvent is preferably used in a proportion of from 5 to 10 equivalents by volume per equivalent by weight of compound of formula (VI).

The reaction is carried out at a temperature of between −20° C. and 25° C.

The reaction thus described takes place over a period of from 4 to 15 hours.

The compound of formula (VI) and the salts thereof are novel and form part of the invention.

According to another of its aspects, a subject of the invention is a process for preparing (+)-[2-[2-(4-amino-4-phenylpiperid-1-yl)ethyl]-2-(3,4-difluorophenyl)morpholin-4-yl]phenylmethanone, or a salt thereof, of formula:

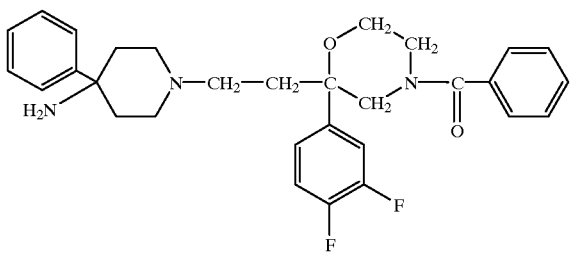

(VI)

characterized in that tert-butyl (+)-(1-{2-[4-benzoyl-2-(3,4-difluorophenyl)morpholin-2-yl]ethyl}-4-phenylpiperid-4-yl)carbamate, of formula:

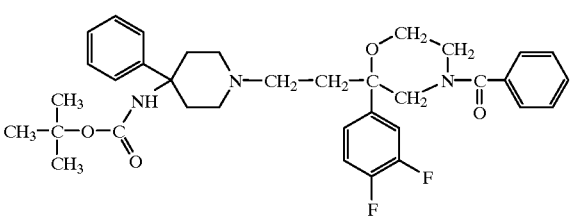

(V)

is deprotected by the action of an acid, in an inert solvent, and the compound of formula (VI) thus obtained is optionally converted into a salt thereof.

A strong acid such as hydrochloric acid, trifluoroacetic acid or formic acid is preferably used to carry out the deprotection. The hydrochloric acid may be generated in situ from acetyl chloride and methanol.

It is particularly preferred to use hydrochloric acid.

The acid is used in the reaction in a proportion of from 4 to 10 molar equivalents per molar equivalent of compound of formula: (V) and preferably from 4 to 6 molar equivalents.

The inert solvent may be, for example, methyl isobutyl ketone, dichloromethane, ethyl acetate, toluene or a mixture of these solvents. Methyl isobutyl ketone is a preferred solvent.

The inert solvent is used in a proportion of from 2 to 15 equivalents by volume per equivalent by weight of compound of formula (V). The solvent is preferably used in a proportion of from 2 to 5 equivalents by volume per equivalent by weight of compound of formula (V).

The reaction is carried out at a temperature of between 10° C. and 60° C., preferably at a temperature of between 20° C. and 40° C.

The reaction takes place over a period of from 30 minutes to 18 hours.

Compound (VI) thus obtained may be subsequently separated from the reaction medium according to the conventional methods.

The compound of formula (VI) obtained is isolated in the form of the free base or of a salt thereof, by using the methods mentioned above for compound A.

The compound of formula (V) and the salts thereof are novel and form part of the invention.

According to another of its aspects, a subject of the invention is a process for preparing tert-butyl (+)-(1-{2-[4-benzoyl-2-(3,4-difluorophenyl)morpholin-2-yl]ethyl}-4-phenylpiperid-4-yl)carbamate, or a salt thereof, of formula:

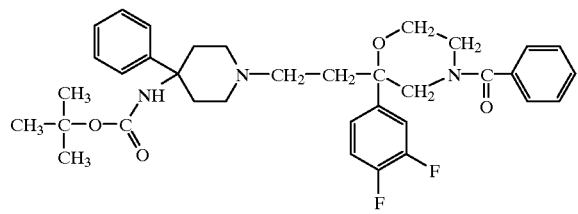

(V)

characterized in that (+)-4-benzoyl-2-(3,4-difluorophenyl)-2-(2-benzenesulfonyloxyethyl)morpholine, of formula:

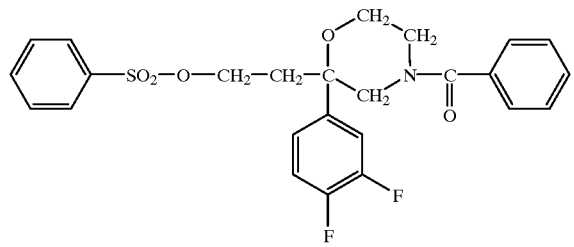

(III)

is reacted with tert-butyl (4-phenylpiperid-4-yl)carbamate, of formula:

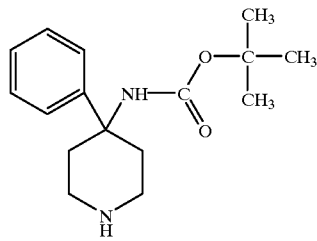

(IV)

in the presence of a base, in an inert solvent as a mixture with water, and the compound of formula (V) thus obtained is optionally converted into a salt thereof.

The compound of formula (IV) is used in the reaction in a proportion of from 1 to 1.25 molar equivalents per molar equivalent of compound of formula (III).

The base used in the reaction is chosen from an alkali metal hydroxide such as sodium hydroxide or potassium hydroxide, or from alkali metal carbonates or bicarbonates such as potassium carbonate, sodium carbonate or sodium bicarbonate. Potassium carbonate is preferably used.

The base is used in the reaction in a proportion of from 1 to 3 molar equivalents per molar equivalent of compound of formula (III).

Water is used in the reaction in a proportion of from 1 to 3 equivalents by volume per equivalent by weight of base.

The inert solvent may be, for example, methyl isobutyl ketone, toluene, acetonitrile, ethanol or a mixture of these solvents. Methyl isobutyl ketone is a preferred solvent.

The inert solvent is used in a proportion of from 2 to 15 equivalents by volume per equivalent by weight of compound of formula (III). The solvent is preferably used in a proportion of from 2 to 5 equivalents by volume per equivalent by weight of compound of formula (III).

The reaction is carried out at a temperature of between 20° C. and 90° C.

The reaction takes place over a period of from 2 to 30 hours.

The compound of formula (V) thus obtained may be subsequently separated from the reaction medium according to the conventional methods.

The compound of formula (V) obtained is isolated in the form of the free base or of a salt thereof, using the methods mentioned above for compound A.

Alternatively, the compound of formula (VI) may also be prepared, in the process according to the invention, directly and in a single step starting with the compound of formula (III), thereby simplifying the process.

According to another of its aspects, a subject of the invention is another process for preparing (+)-[2-[2-(4-amino-4-phenylpiperid-1-yl)ethyl]-2-(3,4-difluorophenyl)morpholin-4-yl]phenylmethanone, or a salt thereof, of formula:

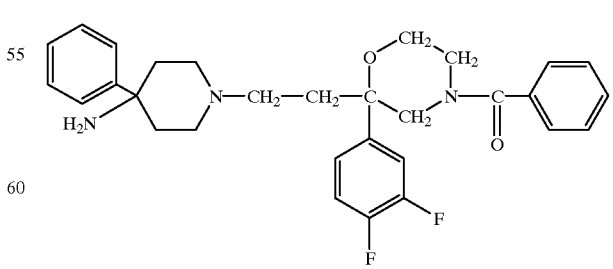

(VI)

characterized in that (+)-4-benzoyl-2-(3,4-difluorophenyl)-2-(2-benzenesulfonyloxyethyl)morpholine of formula:

is reacted with 4-amino-4-phenylpiperidine of formula:

in the presence of a base, in an inert solvent as a mixture with water, and the compound of formula (VI) thus obtained is optionally converted into a salt thereof.

The compound of formula (IX) is used in the reaction in a proportion of from 1 to 1.25 molar equivalents per molar equivalent of compound of formula (III).

The base used in the reaction is chosen from an alkali metal hydroxide such as sodium hydroxide or potassium hydroxide, or from alkali metal carbonates or bicarbonates such as potassium carbonate, sodium carbonate or sodium bicarbonate. Potassium carbonate is preferably used.

The base is used in the reaction in a proportion of from 1 to 3 molar equivalents per molar equivalent of compound of formula (III).

Water is used in the reaction in a proportion of from 1 to 3 equivalents by volume per equivalent by weight of base.

The inert solvent may be, for example, methyl isobutyl ketone, toluene, acetonitrile, ethanol or a mixture of these solvents. Methyl isobutyl ketone is a preferred solvent.

The inert solvent is used in a proportion of from 2 to 15 equivalents by volume per equivalent by weight of compound of formula (III). The solvent is preferably used in a proportion of from 2 to 5 equivalents by volume per equivalent by weight of compound of formula (III).

The reaction is carried out at a temperature of between 20° C. and 90° C.

The reaction takes place over a period of from 2 to 30 hours.

The compound of formula (VI) thus obtained may be subsequently separated from the reaction medium according to the conventional methods.

The compound of formula (VI) obtained is isolated in the form of the free base or a salt thereof, using the methods described above for compound A.

The compound of formula (IV) is known and is prepared according to known methods such as those disclosed in EP-A-0 673 928.

The compound of formula (IX) is known and is prepared according to known methods such as those disclosed in WO 97/10211, in particular by deprotection, according to the conventional methods, of the known 4-amino-1-benzyl-4-phenylpiperidine prepared according to WO 97/10211 or WO 96/23787.

The compound of formula (III) is novel and forms part of the invention.

The compound of formula (III) is prepared according to the known methods such as those disclosed in WO 96/23787.

In particular, the compound of formula (III) is prepared according to the Scheme below.

Scheme 1

In step i), the compound of formula (VII) is reacted with benzoyl chloride, in the presence of a base such as sodium hydroxide, in an inert solvent such as dichloromethane or toluene as a mixture with water and at a temperature of between 10° C. and 35° C. After extraction and washing with water, the compound of formula (VIII) dissolved in the organic phase is reacted (step ii)) with benzenesulfonyl chloride, in the presence of a phase-transfer catalyst such as benzyltriethylammonium chloride, a base such as sodium hydroxide and water and at a temperature of between room temperature and 55° C. After hydrolysis with water, the compound of formula (III) is isolated according to the conventional methods.

The compound of formula (III) may be reacted without being isolated from the medium in which it was produced. The compound of formula (VII) is known and is prepared according to known methods, such as those disclosed in WO 96/23787 or, specifically, in Tetrahedron : Asymmetry, 1998 9, 3251–3262.

The non-limiting examples which follow illustrate the invention.

EXAMPLE 1

(+)-4-Benzoyl-2-(3,4-difluorophenyl)-2-(2-benzenesulfonyloxyethyl)morpholine, Compound of Formula (III).

160 ml of water are added to a mixture of 17.74 g of (+)-2-[2-(3,4-difluorophenyl)morpholin-2-yl]ethanol (compound VII) in 180 ml of dichloromethane, followed by addition of 18.2 ml of a 30% solution of sodium hydroxide in water. The mixture is stirred vigorously and 10.25 g of benzoyl chloride are added rapidly, over 3 minutes, the temperature rising from 20.7° C. to 30.7° C. The mixture is left stirring and the temperature is allowed to return to 27° C. After separation of the phases by settling, the aqueous phase is extracted with 5 ml of dichloromethane and the organic phases containing compound (VIII) are combined.

The combined organic phases are stirred at 350 rpm and 0.85 g of benzyltriethylammonium chloride is added, followed by addition of a solution of 27 g of sodium hydroxide in 27 ml of water, the temperature rising to 30° C. 25.8 g of benzenesulfonyl chloride are then added rapidly, the temperature rising slowly to 34.7° C., and the mixture is left stirring for 18 hours and maintained at a temperature of 32° C. The reaction mixture is hydrolyzed by adding 200 ml of water and, after separation of the phases by settling, the organic phase is then concentrated under vacuum. The residue is taken up in 200 ml of toluene and the organic phase is washed successively with 100 ml of water, twice with 100 ml of pH 2 sulfate buffer, with 100 ml of water and with 100 ml of saturated sodium chloride solution and dried over magnesium sulfate and, after filtration, the solvent is evaporated off under vacuum. The oil obtained is taken up in 100 ml of diisopropyl ether, the solvent is evaporated off again under vacuum, and this operation is repeated entirely three times. The product obtained is taken up in 100 ml of a diisopropyl ether/diethyl ether mixture (50/50; v/v) cooled to 0° C. and left to solidify for 2 hours. This mixture is left overnight at room temperature, cooled to 0° C. for 1 hour and the precipitate formed is spin-filtered off and dried under vacuum. 31.6 g of the expected product are obtained.

Yield: 89%. Melting point: 82.8° C. $\alpha_D^{20}$=+46.9° (c=1; MeOH).

EXAMPLE 2 tert-Butyl (+)-(1-{2-[4-Benzoyl-2-(3,4-difluorophenyl)morpholin-2-yl]ethyl}-4-phenylpiperid-4-yl)carbamate, Compound of Formula (V).

A solution of 18 g of potassium carbonate in 18 ml of water is added to a mixture of 22.6 g of tert-butyl (4-phenylpiperid-4-yl)carbamate hydrochloride (compound (IV)) and 30 g of compound of formula (III) obtained in Example 1 in 300 ml of acetonitrile, and the mixture is then heated at 70° C. for 12 hours and left overnight at room temperature. The acetonitrile is concentrated under vacuum, the residue is taken up in 300 ml of dichloromethane, the organic phase is washed successively with 150 ml of a 0.3 M solution of sodium hydroxide in water, with 150 ml of water, twice with 150 ml of pH 2 sulfate buffer, with 150 ml of water and with 150 ml of a 10% by weight solution of potassium carbonate in water, dried over magnesium sulfate and filtered, and the solvent is evaporated off under vacuum at room temperature. The expected product is obtained, which is used in Example 3.

Melting point: 106.8° C. $\alpha_D^{20}$=+16.2° (c=1; MeOH);

EXAMPLE 3

(+)-[2-[2-(4-Amino-4-phenylpiperid-1-yl)ethyl]-2-(3,4-difluorophenyl)morpholin-4-yl] phenylmethanone dihydrochloride, Compound of Formula (VI).

250 ml of methanol are cooled to −10° C., 25 ml of acetyl chloride are added rapidly and the solution is allowed to return to room temperature. The compound of formula (V) obtained in Example 2 is then added and is left stirring overnight at room temperature. The solvent is concentrated under vacuum at room temperature, the residue is taken up in 100 ml of methanol and the solvent is concentrated again under vacuum. The residue is taken up in 100 ml of ethyl acetate and the solvent is concentrated under vacuum, and this operation is repeated entirely three times. The residue is taken up in 150 ml of ethyl acetate and left stirring for two hours at room temperature, and the precipitate formed is spin-filtered off, washed with ethyl acetate and dried under vacuum. 32.4 g of the expected product are obtained.

Yield: 91% (calculated on the basis of compound (III)); Melting point: 272.2° C. $\alpha_D^{20}$ (free base)=+17.6° (c=1; MeOH).

EXAMPLE 3a (+)-[2-[2-(4-Amino-4-phenylpiperid-1-yl)ethyl]-2-(3,4-difluorophenyl)morpholin-4-yl] phenylmethanone, Compound of Formula (VI)

4-Amino-4-phenylpiperidine.

3.2 ml of 12N hydrochloric acid solution are added to a solution of 5 g of 4-amino-1-benzyl-4-phenylpiperidine in 25 ml of methanol, followed by addition of 0.5 g of 10% palladium-on-charcoal (50% water) and hydrogen overnight, at atmospheric pressure and at 40° C. The catalyst is filtered off and the filtrate is concentrated under vacuum. The residue is taken up in 15 ml of water, basified by addition of 3.8 ml of 10N sodium hydroxide solution and left stirring. Sodium chloride crystals are added to the aqueous phase and the mixture is extracted twice with 25 ml of dichloromethane. The organic phase is dried over sodium sulfate and filtered, and the solvent is evaporated off under vacuum. 3.4 g of the expected product are obtained. b) A solution of 2.83 g of potassium carbonate in 2.8 ml of water is added to a solution of 4 g of compound of formula (III) obtained in Example 1 in 9.2 ml of toluene and 8 ml of methyl isobutyl ketone, followed by addition of 1.6 g of 4-amino-4-phenylpiperidine, and this mixture is heated at 70° C. for 12 hours. After cooling the reaction mixture to room temperature, 16 ml of water are added and the phases are then separated by settling. The organic phase is washed twice with 16 ml of water and is acidified by adding a solution of 1.5 ml of 12N hydrochloric acid in 16 ml of water, and the phases are then separated by settling. The acidic aqueous phase is washed twice with 10 ml of toluene, the aqueous phase is basified by adding 2 ml of 10N sodium hydroxide solution and is extracted twice with 30 ml of toluene. The organic phase is dried over magnesium sulfate and filtered, and the solvent is evaporated off under vacuum. 4 g of the expected product are obtained in the form of an oil.

EXAMPLE 4

(R)-(+)-3-{1-[2-(4-Benzoyl-2-(3,4-difluorophenyl)morpholin-2-yl)ethyl]-4-phenylpiperid-4-yl}-1,1-dimethylurea Fumarate, Compound A 100 ml of a solution containing 20% by weight of potassium carbonate are added to a suspension of 32.3 g of the compound of formula (VI) obtained in Example 3 in 150 ml of dichloromethane, and the mixture is stirred vigorously. After separation of the phases by settling, the aqueous phase is extracted with 50 ml of dichloromethane, the organic phases are combined, dried over magnesium sulfate and filtered, and 16.5 ml of triethylamine are added to this solution. This solution is then added, under a nitrogen atmosphere, over two hours 15 minutes and while maintaining the temperature of the reaction medium between −8° C. and −10° C., to 42 ml of a 1.4M solution of phosgene in toluene cooled beforehand to −10° C., and the mixture is then stirred for 30 minutes at −10° C. 5 ml of a 1.4M solution of phosgene in toluene are added rapidly, the mixture is stirred for 5 minutes and a further 1 ml of a 1.4M solution of phosgene in toluene is added. 50 ml of a 2M solution of dimethylamine in tetrahydrofuran are then added, over 3 minutes at −12° C., and the mixture is then stirred while allowing the temperature to return to room temperature. The reaction mixture is poured into 200 ml of pH 2 sulfate buffer and, after separation of the phases by settling, the organic phase is washed successively with 200 ml of pH 2 sulfate buffer, with 200 ml of water, with 200 ml of a 10% solution of potassium carbonate in water, dried over magnesium sulfate and filtered, and the filtrate is concentrated under vacuum. The residue is dissolved in 50 ml of acetone and this solution is poured onto a mixture of 6.4 g of fumaric acid in 256 ml of acetone, heated to reflux beforehand. After the addition, the medium is kept stirring at 57° C. for 15 minutes and then allowed to cool to 26° C. The precipitate formed is spin-filtered off, washed twice with 50 ml of acetone and dried under vacuum overnight at room temperature. 29.1 g of compound A are thus obtained in the form of the fumarate.

Yield: 75% (calculated on the basis of compound VI) 68.25% (calculated on the basis of compound III). Melting point: 201.5° C. $\alpha_D^{20}$=+19.1° (c=1; MeOH).

EXAMPLE 5

(R)-(+)-3-{1-[2-(4-Benzoyl-2-(3,4-difluorophenyl) morpholin-2-yl)ethyl]-4-phenylpiperid-4-yl}-1,1-dimethylurea Succinate, Compound A a) 58 g of tert-butyl (4-phenylpiperid-4-yl)carbamate (compound IV)) are added with stirring to a mixture of 92.6 g of compound of formula (III) in 200 ml of methyl isobutyl ketone, a solution of 31.6 g of potassium carbonate in 32 ml of water is then added and the mixture is heated at 70° C. for 23 hours with stirring. The reaction mixture is cooled to 50° C., 460 ml of water are added over 1 hour, this mixture is cooled to 30° C. and the phases are separated by settling. The organic phase containing the compound of formula (V) is used directly in the following step.

b) The solution of the compound of formula (V) in methyl isobutyl ketone obtained in step a) is heated to 30° C. with stirring, and 80 ml of a 12M solution of hydrochloric acid in water are then added dropwise over 45 minutes. At the end of the addition, 380 ml of water are added to the reaction mixture, the phases are separated by settling, the organic phase is discarded, the aqueous phase is washed with 380 ml of ethyl acetate and is basified by adding 115 ml of a 10M solution of sodium hydroxide in water and is extracted with 380 ml of toluene, and the organic phase is washed four times with 380 ml of water. 380 ml of water are added to the organic phase, the mixture is acidified by adding 32 ml of a 12M solution of hydrochloric acid in water, the organic phase is discarded, the aqueous phase is basified by adding 42 ml of a 10M solution of sodium hydroxide in water and is extracted three times with 380 ml of dichloromethane. The organic phase is dried over magnesium sulfate and filtered, and the filtrate is concentrated under vacuum to a final solution weight of 330 g. The organic phase containing the compound of formula (VI) is used in the following step.

c) A suspension of 60.7 g of 1,1'-carbonyldiimidazole in 607 ml of dichloromethane is cooled to 0° C. and the solution of compound of formula (VI) in dichloromethane obtained in step b) is added dropwise over 3 hours with stirring, under a nitrogen atmosphere, while maintaining the temperature of the reaction medium at 0° C. At the end of the addition, the reaction mixture is cooled to 0° C. and 32.8 g of dimethylamine gas are added over 45 minutes, with stirring, by sparging. The temperature of the reaction medium rises to 10° C., and is 3° C. at the end of the addition. The reaction mixture is allowed to return to 20° C. with stirring, 1000 ml of water are then added, the mixture is left stirring for 15 minutes and the aqueous phase is removed, and this operation is repeated three times. The organic phase is dried over magnesium sulfate and filtered, and the solvent is evaporated off under vacuum. 112.6 g of an oil containing 78% by weight of compound A are obtained.

d) A solution of 10.5 g of succinic acid in 425 ml of acetone is added, over a few minutes at room temperature, to a solution of 65.9 g of the above oil (i.e. 51.4 g of compound A) in 52 ml of acetone, and the mixture is then stirred for 24 hours. The precipitate formed is spin-filtered off, washed three times with 50 ml of acetone and dried overnight under vacuum at room temperature. 48.7 g of compound A are obtained in the form of the succinate. Salification yield: 78.7%

Overall yield: 63.1% (calculated on the basis of the compound III). Melting point: 155° C. $\alpha_D^{20}$=+17.50 (c=1; MeOH).

What is claimed is:

1. A process for preparing (R)-(+)-3-{1-[2-(4-benzoyl-2-(3,4-difluorophenyl)morpholin-2-yl)ethyl]-4-phenylpiperid-4-yl}1,1-dimethylurea, and the salts, solvates and/or hydrates thereof, of formula:

(I)

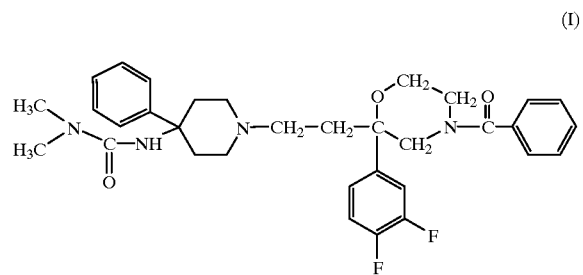

wherein (+)-[2- [2-(4-amino-4-phenylpiperid-1yl)ethyl]-2-(3,4-difluoro-phenyl)morpholin-4-yl]phenylmethanone, of formula:

(VI)

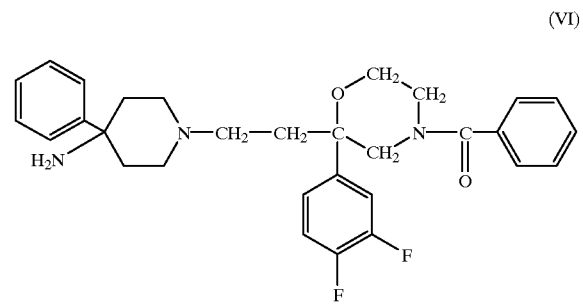

is reacted, in an inert solvent, first with a reactive derivative of carbonic acid in the presence or absence of base, and then with dimethylamine, and the compound of formula (I) thus obtained is optionally converted into a salt thereof with pharmaceutically acceptable mineral or organic acids.

2. A process according to claim 1 wherein the reactive derivative of carbonic acid is chosen from 1,1'-carbonyldiimidazole, phosgene and p-nitrophenyl chloroformate.

3. A process according to claim 2 wherein the reactive derivative of carbonic acid is used in a proportion of from 1 to 3 molar equivalents per molar equivalent of compound of formula (VI).

4. A process according to claim 3 wherein when phosgene or p-nitrophenyl chloroformate is used, the reaction is carried out in the presence of a base chosen from triethylamine, N,N-diisopropylethylamine and N-methylmorpholine.

5. A process according to claim 4 wherein the base is used in a proportion of from 1 to 6 molar equivalents per molar equivalent of reactive derivatives of carbonic acid.

6. A process according to claim 5 wherein the dimethylamine is used in a proportion of from 1 to 6 molar equivalents per molar equivalent of compound of formula (VI).

7. A process according to claim 6 wherein the inert solvent is dichloromethane, 1,2-dichloroethane, chloroform or carbon tetrachloride.

8. A process according to claim 7 wherein the reaction is carried out at a temperature of between −20° C. and 25° C.

9. A process according to claim 1 wherein (+)-[2-[2-(4-amino-4-phenylpiperid-1-yl)ethyl]-2-(3,4-difluorophenyl)morpholin-4-yl]phenylmethanone, or a salt thereof, of formula:

(VI)

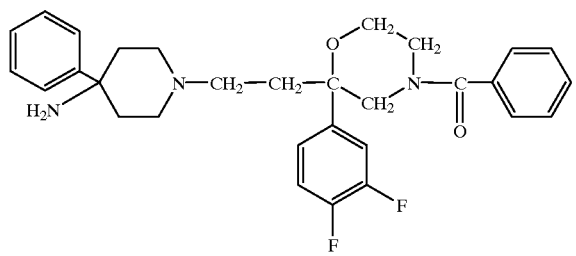

is prepared by reacting tert-butyl (+)-(1-{2-[4-benzoyl-2-(3,4-difluorophenyl)morpholin-2-yl]ethyl }-4-phenylpiperid-4-yl)carbamate, of formula:

(V)

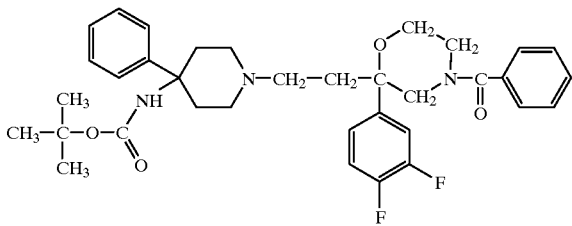

with an acid, in an inert solvent, and the compound of formula (VI) thus obtained is optionally converted into a salt thereof.

10. A process according to claim 9 wherein the acid is hydrochloric acid, trifluoroacetic acid or formic acid.

11. A process according to claim 10 wherein the acid is used in a proportion of from 4 to 10 molar equivalents per molar equivalent of compound of formula (V).

12. A process according to claim 11 wherein the inert solvent is methyl isobutyl ketone, dichloromethane, ethyl acetate, toluene or a mixture of these solvents.

13. A process according to claim 12 wherein the reaction is carried out at a temperature of between 10° C. and 60° C.

14. A process according to claim 9 wherein tert-butyl (+)-(1-{2-[4-benzoyl-2-(3,4-difluorophenyl)morpholin-2-yl]ethyl }-4-phenylpiperid-4-yl)carbamate, or a salt thereof, of formula:

(V)

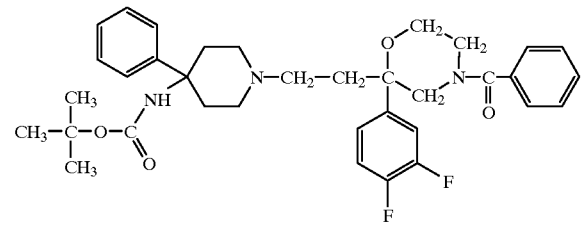

is prepared by reacting (+)-4-benzoyl-2-(3,4-difluorophenyl)-2-(2-benzenesulfonyloxy-ethyl)morpholine of formula:

(III)

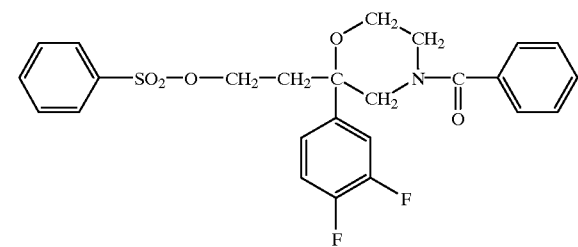

with tert-butyl (4-phenylpiperid-4-yl)carbamate, of formula:

(IV)

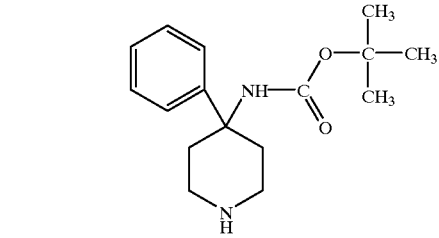

in the presence of a base, in an inert solvent as a mixture with water, and the compound of formula (V) thus obtained is optionally converted into a salt thereof.

15. A process according to claim 14 wherein the compound of formula (IV) is used in a proportion of from 1 to 1.25 molar equivalents per molar equivalent of compound of formula (III).

16. A process according to claim 15 wherein the base is an alkali metal hydroxide or an alkali metal carbonate or bicarbonate.

17. A process according to claim 16 wherein the base is used in a proportion of from 1 to 3 molar equivalents per molar equivalent of compound of formula (III).

18. A process according to claim 17 wherein water is used in a proportion of from 1 to 3 equivalents by volume per equivalent by weight of base.

19. A process according to claim 18 wherein the inert solvent is methyl isobutyl ketone, toluene, acetonitrile, ethanol or a mixture of these solvents.

20. A process according to claim 19 wherein the reaction is carried out at a temperature of between 20° C. and 90° C.

21. A process according to claim 1 wherein (+)-[2-[2-(4-amino-4-phenylpiperid-1-yl)ethyl]-2-(3,4-difluorophenyl)morpholin-4-yl]phenylmethanone, or a salt thereof, of formula:

(VI)

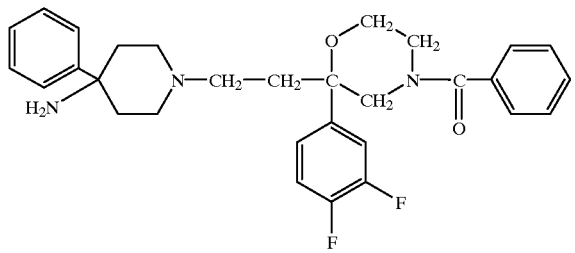

is prepared by reacting (+)-4-benzoyl-2-(3,4-difluorophenyl)-2-(2-benzenesulfonyloxy-ethyl)morpholine of formula:

(III)

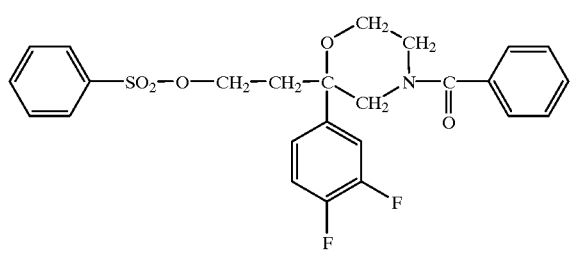

with 4-amino-4-phenylpiperidine of formula:

(IX)

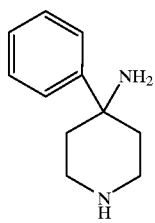

in the presence of a base, in an inert solvent as a mixture with water, and the compound of formula (VI) thus obtained is optionally converted into a salt thereof.

22. A process according to claim 21 wherein the compound of formula (IX) is used in a proportion of from 1 to 1.25 molar equivalents per molar equivalent of compound of formula (III).

23. A process according to claim 22 wherein the base is an alkali metal hydroxide or an alkali metal carbonate or bicarbonate.

24. A process according to claim 23 wherein the base is used in a proportion of from 1 to 3 molar equivalents per molar equivalent of compound of formula (III).

25. A process according to claim 24 wherein water is used in a proportion of from 1 to 3 equivalents by volume per equivalent by weight of base.

26. A process according to claim 25 wherein the inert solvent is methyl isobutyl ketone, toluene, acetonitrile, ethanol or a mixture of these solvents.

27. A process according to claim 26 wherein the reaction is carried out at a temperature of between 20° C. and 90° C.

28. A process for preparing (+)-[2-[2-(4-amino-4-phenylpiperid-1-yl)ethyl]-2-(3,4-difluorophenyl)morpholin-4-yl]phenylmethanone, or a salt thereof, of formula:

(VI)

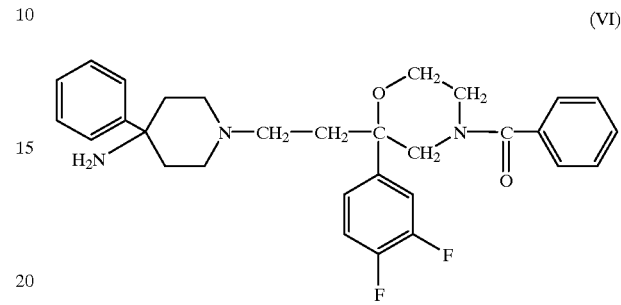

wherein tert-butyl (+)-(1-{2-[4-benzoyl-2-(3,4-difluorophenyl)morpholin-2-yl]ethyl}-4-phenyl-piperid-4-yl)carbamate, of formula:

(V)

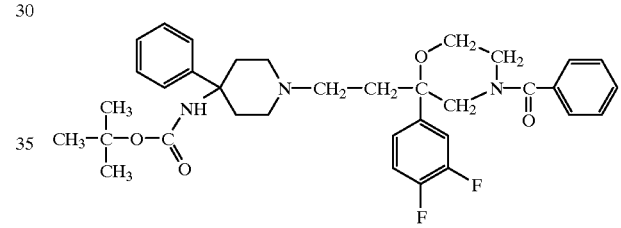

is deprotected by the action of an acid, in an inert solvent, and the compound of formula (VI) thus obtained is optionally converted into a salt thereof.

29. A process according to claim 28 wherein tert-butyl (+)-(1-{2-[4-benzoyl-2-(3,4-difluorophenyl)morpholin-2-yl]ethyl}-4-phenylpiperid-4-yl)carbamate, or a salt thereof, of formula:

(V)

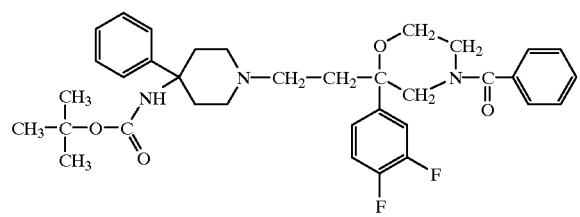

is prepared by reacting (+)-4-benzoyl-2-(3,4-difluorophenyl)-2-(2-benzenesulfonyloxy-ethyl)morpholine, of formula:

with tert-butyl (4-phenylpiperid-4-yl)carbamate, of formula:

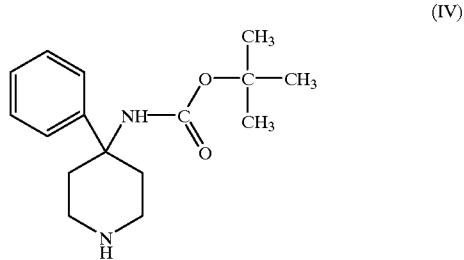
(IV)

in the presence of a base, in an inert solvent as a mixture with water, and the compound of formula (V) thus obtained is optionally converted into a salt thereof.

30. A process for preparing tert-butyl (+)-(1-{2-[4-benzoyl-2-(3,4-difluoro-phenyl)morpholin-2-yl]ethyl}-4-phenylpiperid-4-yl)carbamate, or a salt thereof, of formula:

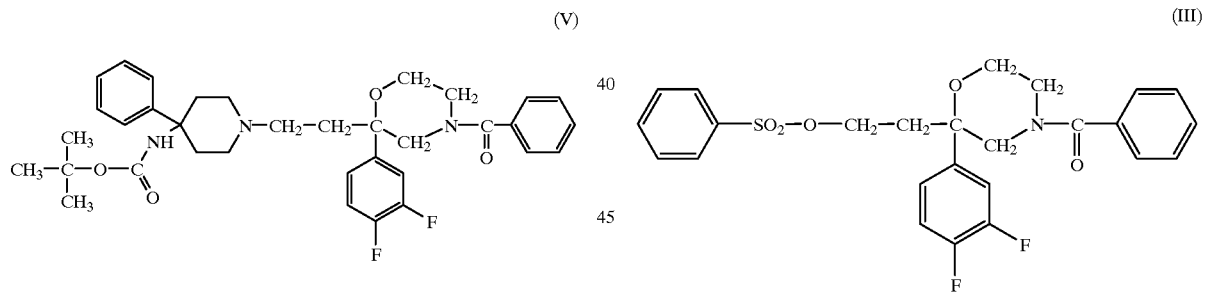
(V)

wherein (+)-4-benzoyl-2-(3,4-difluorophenyl)-2-(2-benzenesulfonyloxyethyl)morpholine, of formula:

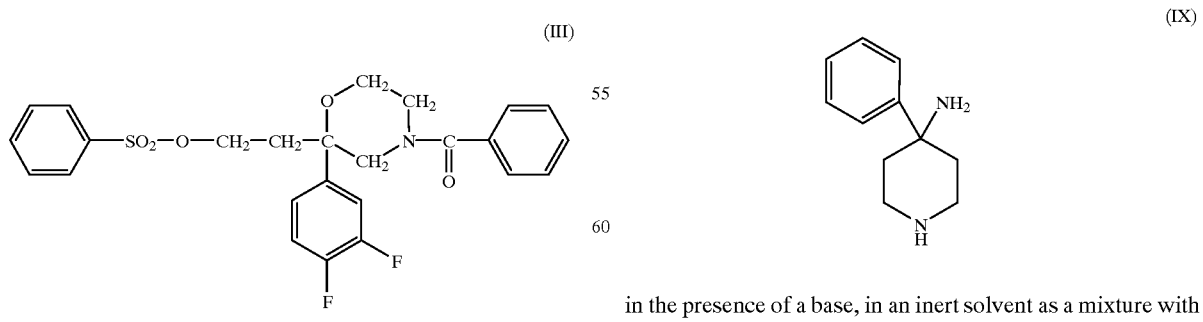
(III)

is reacted with tert-butyl (4-phenylpiperid-4-yl)carbamate, of formula:

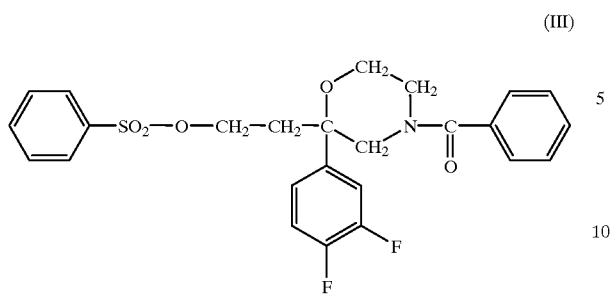
(III)

in the presence of a base, in an inert solvent as a mixture with water, and the compound of formula (V) thus obtained is optionally converted into a salt thereof.

31. A process for preparing (+)-[2-[2-(4-amino-4-phenylpiperid-1-yl)ethyl]-2-(3,4-difluorophenyl)morpholin-4-yl]phenylmethanone, or a salt thereof, of formula:

(VI)

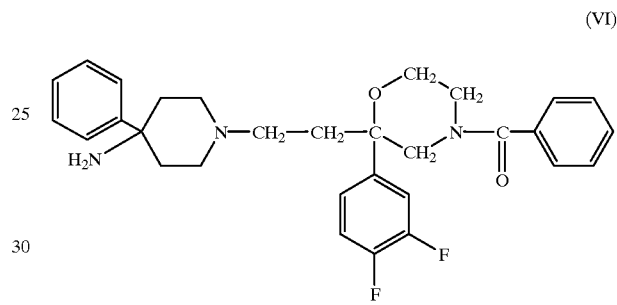

wherein (+)-4-benzoyl-2-(3,4-difluorophenyl)-2-(2-benzenesulfonyloxyethyl)morpholine, of formula:

(III)

is reacted with 4-amino-4-phenylpiperidine of formula:

(IX)

in the presence of a base, in an inert solvent as a mixture with water, and the compound of formula (VI) thus obtained is optionally converted into a salt thereof.

32. (+)-[2-[2-(4-Amino-4-phenylpiperid-1-yl)ethyl]-2-(3,4-difluorophenyl)morpholin-4-yl)phenylmethanone, and the salts thereof, of formula:

(VI)

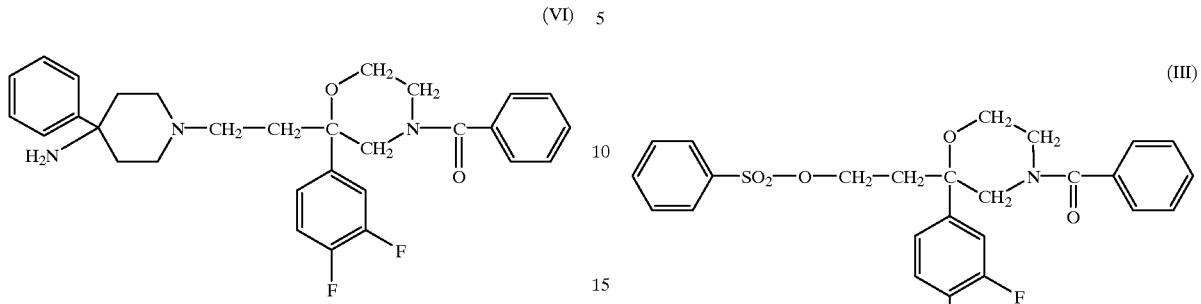

33. tert-Butyl (+)-(1-{2-[4-benzoyl-2-(3,4-difluorophenyl)morpholin-2-yl]ethyl}-4-phenylpiperid-4-yl)carbamate, and the salts thereof, of formula:

(V)

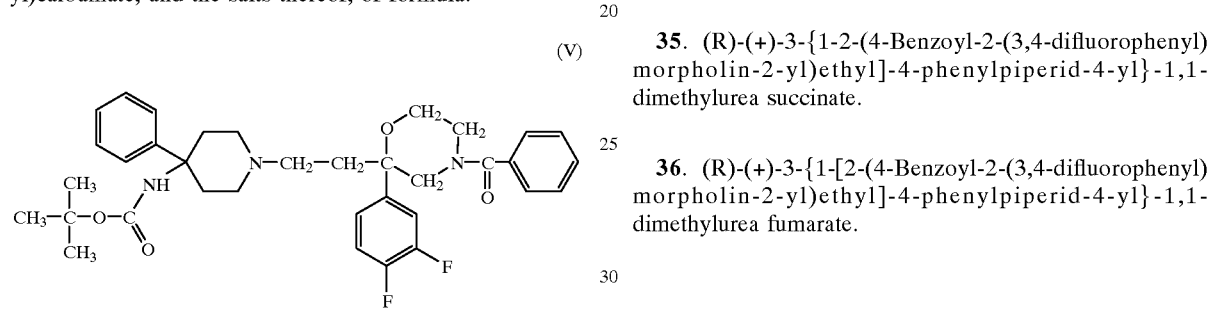

34. (+)-4-Benzoyl-2-(3,4-difluorophenyl)-2-(2-benzenesulfonyloxyethyl)morpholine of formula:

(III)

35. (R)-(+)-3-{1-2-(4-Benzoyl-2-(3,4-difluorophenyl)morpholin-2-yl)ethyl]-4-phenylpiperid-4-yl}-1,1-dimethylurea succinate.

36. (R)-(+)-3-{1-[2-(4-Benzoyl-2-(3,4-difluorophenyl)morpholin-2-yl)ethyl]-4-phenylpiperid-4-yl}-1,1-dimethylurea fumarate.

* * * * *